United States Patent
Adriansens et al.

(10) Patent No.: US 8,092,757 B2
(45) Date of Patent: Jan. 10, 2012

(54) METHOD FOR STERILIZING PREFORMS AND INSTALLATION FOR PRODUCING STERILE BODIES FROM THESE PREFORMS

(75) Inventors: Eric Adriansens, Octeville sur Mer (FR); Stéphane Hebert, Octeville sur Mer (FR)

(73) Assignee: Sidel Participations, Octeville-sur-Mer (FR)

( * ) Notice: Subject to any disclaimer, the term of this patent is extended or adjusted under 35 U.S.C. 154(b) by 560 days.

(21) Appl. No.: 11/993,494

(22) PCT Filed: Jun. 8, 2006

(86) PCT No.: PCT/EP2006/063006
§ 371 (c)(1),
(2), (4) Date: Feb. 13, 2008

(87) PCT Pub. No.: WO2006/136499
PCT Pub. Date: Dec. 28, 2006

(65) Prior Publication Data
US 2010/0047120 A1    Feb. 25, 2010

(30) Foreign Application Priority Data
Jun. 24, 2005  (FR) .................................. 05 51752

(51) Int. Cl.
*A01H 5/02* (2006.01)
*B29D 5/00* (2006.01)
*B29C 49/00* (2006.01)
(52) U.S. Cl. .................. 422/309; 264/252; 425/524
(58) Field of Classification Search .......... 422/309; 264/252; 425/524
See application file for complete search history.

(56) References Cited

U.S. PATENT DOCUMENTS

| 4,512,591 | A | 4/1985 | Plante |
| 6,039,922 | A | 3/2000 | Swank et al. |
| 6,562,281 | B1 * | 5/2003 | Marchau et al. ............. 264/532 |
| 6,692,684 | B1 | 2/2004 | Nantin et al. |
| 6,919,043 | B2 * | 7/2005 | Hayakawa et al. ............ 422/28 |
| 6,984,360 | B1 * | 1/2006 | Feuilloley et al. ............ 422/28 |
| 7,186,374 | B2 * | 3/2007 | Zelina et al. .................... 422/28 |

(Continued)

FOREIGN PATENT DOCUMENTS
DE    19949692    4/2001
(Continued)

OTHER PUBLICATIONS

JP Office Action (translation) dated Oct. 8, 2010 from JP2008-517457.

(Continued)

*Primary Examiner* — Walter Griffin
*Assistant Examiner* — Christopher Vandeusen
(74) *Attorney, Agent, or Firm* — Young & Thompson (57) ABSTRACT

A sterilization method and an installation for producing sterile bottles by blow molding sterilized preforms includes, at the spraying station, the flow of sterilizing product atomized onto each preform whose temperature (T1) is less than the condensing temperature (Tc) of the sterilizing product so that a film of mist of the sterilizing product deposits by condensation at least onto the inner wall to be sterilized, and, at the activation station of the sterilizing product of the sterilizing unit, each preform treated in the aforementioned manner is heated by radiation to a temperature (T2) greater than or equal to the activation temperature (Ta) in order to sterilize at least the inner wall of the preform.

4 Claims, 3 Drawing Sheets

U.S. PATENT DOCUMENTS

| | | | |
|---|---|---|---|
| 2001/0010145 A1* | 8/2001 | Tawa et al. | 53/425 |
| 2002/0159915 A1* | 10/2002 | Zelina et al. | 422/3 |
| 2003/0165400 A1* | 9/2003 | Hayakawa et al. | 422/28 |
| 2005/0118057 A1* | 6/2005 | Quetel et al. | 422/24 |
| 2005/0226796 A1* | 10/2005 | Hayakawa et al. | 422/302 |

FOREIGN PATENT DOCUMENTS

| | | |
|---|---|---|
| EP | 1 122 168 | 8/2001 |
| FR | 2 766 169 | 1/1999 |
| JP | 10323385 | 12/1998 |
| JP | 11059629 | 3/1999 |
| JP | 03 290226 | 12/1999 |
| JP | 2003512260 | 4/2001 |
| JP | 2004528886 | 9/2002 |
| WO | WO 99/03667 | 1/1999 |
| WO | 0128863 A1 | 4/2001 |
| WO | 02074351 A1 | 9/2002 |

OTHER PUBLICATIONS

Translation of JP Office Action Patent Application No. 2008-517457 mailed Jun. 7, 2011.

* cited by examiner

METHOD FOR STERILIZING PREFORMS AND INSTALLATION FOR PRODUCING STERILE BODIES FROM THESE PREFORMS

The invention relates to a method of sterilizing preforms and to an installation producing sterile bottles from the preforms sterilized by this method.

The invention relates more particularly to a method of sterilizing a plastic preform intended to be molded, especially by blow molding, in an installation producing sterile bottles.

The invention also relates to an installation for producing sterile bottles from plastic preforms by implementing the method of sterilizing preforms according to the invention, of the type in which the preforms are conveyed inside the installation as a continuous flow, which runs from the upstream end toward the downstream end, and of the type comprising, in succession, at least:

- a sterilization unit having at least one spray station provided with at least one nozzle for spraying, during the treatment, a flow of sterilizing agent in the form of a vapor jet toward the neck of each preform to be sterilized; and
- a forming unit comprising a thermal conditioning station, which includes an oven intended to bring each preform to a molding temperature, and a molding station capable of producing a sterile bottle.

Such a type of installation is described and shown in particular in document US-A-2001/0010145.

This type of installation has the drawback of requiring a high flow rate of sterilizing agent and/or a high pressure for injecting the sterilizing agent in order to succeed in completely covering the internal walls of the preforms, so as to completely sterilize the inside of the preforms.

As a consequence, the installation therefore consumes a large amount of sterilizing agent and the sterilization operation is expensive.

In addition, the use of a high flow rate of sterilizing agent may result in residual droplets of sterilizing agent being deposited on the internal walls of the preforms. Now, when the preforms are being heated, these droplets produce a magnifying glass effect on the thermal heating radiation, resulting in the appearance of stains on the walls of the bottles obtained from the preforms in question.

Specifically, in the installations of the prior art, the sterilizing agent is generally sprayed in the form of a mist and with a pressure obtained by compressing a gas, such as air compressed to pressures of about 2 to 3 bar, which is sterilized and heated, for example to a temperature sterile of around 130° C. so as to thermally activate the sterilizing agent.

This is the reason why droplets of sterilizing agent form an excess which is not entirely vaporized during heating, so that each droplet causes a local chemical attack of the preform material, generally polyethylene terephthalate (PET), by the sterilizing agent.

This phenomenon causes stains to appear on the walls of the bottles, this visual defect being sometimes called "orange peel" defect.

In addition, the walls of the preforms are not uniformly covered by the droplets of sterilizing agent, so that regions between each of the droplets on the surface of the internal and/or external walls of the preform remain unsterilized.

Furthermore, depending on the profile of the internal wall of each preform, it is not always possible to reliably reach the bottom of the preforms, even with a high flow rate and/or a high pressure, because of the creation of an overpressure plug at the bottom of the preforms.

Such a type of installation is also described and shown in document WO-A2-99/03667, which relates to a method for manufacturing sterile plastic containers and to an installation for implementing it.

The installation includes a device for bringing preforms to heating means, upstream of which device the preforms are treated, at least on the inside of the preforms, by sterilization means.

The sterilization means comprise in particular a sterilization agent, such as a chemical solution of hydrogen peroxide ($H_2O_2$) that can be thermally actuated, especially through the heat of the heating means, before being eliminated by evaporation.

The sterilization means include, for this purpose, a sprayer formed by a spray gun that allows the inside of the preforms to be wetted with "cold" sterilization agent, that is to say one that has not been preheated and is therefore in the liquid state.

In the installation described in that document, the spray gun is typically a gun of the two-fluid type, having a liquid nozzle and an air nozzle which together form a circular spray assembly which can be placed above the path of the preforms so as to spray a mist of sterilization agent.

The spray of sterilization agent is formed as a cloud of droplets that is sprayed by the spray gun onto the inside of the preform as a turbulent flow.

It has been found that such a turbulent flow of sterilization or sterilizing agent inside the preform results in the formation of a number of droplets that are not uniformly distributed over the internal wall of the preform.

This is because the use of a spray gun is characterized in particular by a high flow rate of sterilizing agent, obtained by compressing a gas, such as air compressed to pressures of about 2 to 3 bar, so that it produces a turbulent flow.

Now, a turbulent flow results in nonuniform deposition of residual droplets of sterilizing agent on the internal walls of the preforms. In addition, the droplets of sterilizing agent form an excess that is not entirely vaporized during heating.

These droplets of sterilizing agent therefore cause, on the one hand, local chemical attack of the material of the preform, generally polyethylene terephthalate (PET), and, on the other hand, while the preforms are being heated, produce a magnifying glass effect on the thermal heating radiation, thereby causing the appearance of stains on the walls of the bottles obtained from the treated preforms.

The appearance of such stains on the walls of the bottles is a visual defect of the product, giving the walls what is still sometimes called an "orange peel appearance".

The present object of the present invention is therefore to remedy these drawbacks and in particular to propose a sterilization method and an installation that are simple and inexpensive.

For this purpose, the invention provides a sterilization method of the type described above, characterized in that it comprises at least the steps consisting, in succession:

(a) in checking that the preform is at a temperature below the temperature of condensation of the sterilizing product;
(b) in spraying a flow of sterilizing agent in the form of a vapor jet onto the preform so as to cause a substantially uniform film of a mist of the sterilizing agent to be deposited by condensation on at least one internal wall of the preform to be sterilized; and
(c) in radiatively heating the preform thus treated in order to bring it to a temperature equal to or above the temperature for activating the sterilizing agent so as to sterilize at least the internal wall of the preform.

Advantageously, the sterilization method includes an additional sterilization step consisting: (d) in spraying a flow of sterilizing agent in the form of a jet of vapor onto the preform preheated to a specified temperature.

Advantageously, the temperature to which the preform is heated is substantially equal to the temperature at which the preform is blow-molded, which temperature is respectively above the activation temperature and above the evaporation temperature in order to eliminate the sterilizing agent by evaporation.

The invention also provides an installation of the type described above, characterized in that, at the first, spray station, the flow of sterilizing agent is vaporized on each preform, the temperature of which is below the condensation temperature of the sterilizing agent so that a substantially uniform film of a mist of the sterilizing agent is deposited by condensing on the internal wall to be sterilized, and in that the sterilization unit includes an activation station for activating the sterilizing agent, comprising radiative heating means constituting the oven for heating each preform thus treated to a temperature equal to or above the activation temperature so as to sterilize at least the internal wall of the preform.

According to other features of the invention:
the heating means of the activation station consist of the oven of the thermal conditioning station so that each preform is heated to a molding temperature which is respectively above the activation temperature of the sterilizing agent and above the evaporation temperature in order to eliminate the sterilizing agent by evaporation;
the molding station of the forming unit includes at least one mold and at least one associated blowing device which subjects each preform to an internal overpressure so that each sterilized preform takes the form of the impression of the mold in order to produce the sterile bottle;
the mean spray axis (A2) along which the nozzle for vaporizing the sterilizing agent sprays the latter toward the neck is generally parallel to the axis (A1) of the preform during treatment and radially offset relative to the axis (A1) of the preform so as to produce a laminar flow of sterilizing agent inside the preform;
in the sterilization unit, the preforms are generally aligned along a longitudinal run direction (X1) and are placed in the upright position, so as to be mutually parallel side by side, and in that the spray axis (A2) of the nozzle is radially offset along a direction approximately orthogonal to the run direction (X1);
the sterilizing agent consists of a compound containing hydrogen peroxide or vaporized hydrogen peroxide, which is activated by heating the preform above the activation temperature;
the sterilizing agent comprising hydrogen peroxide is sprayed in the vapor state at a temperature above one hundred and six degrees Celsius.
the installation is of the type comprising at least one transport device provided with means for gripping the neck of each preform in order to convey the flow of preforms through the oven, which comprises at least one means, such as an internal core, which penetrates axially into the neck of each preform, partly or completely obstructing the inner opening bounded by the neck so as to increase the degree of sterilization by increasing the time during which the internal wall of the preform is exposed to the sterilizing agent; and
the sterilization unit includes, downstream of the oven, another spray station, called the second station, which is intended to spray a second flow of sterilizing agent onto each preform preheated to a defined temperature which is at least above the activation temperature and above the evaporation temperature of the sterilizing agent.

Other features and advantages of the invention will become apparent on reading the following detailed description, for the understanding of which reference will be made to the appended drawings in which.

In the rest of the description, similar or identical elements will be denoted by the same references.

Figure 1:
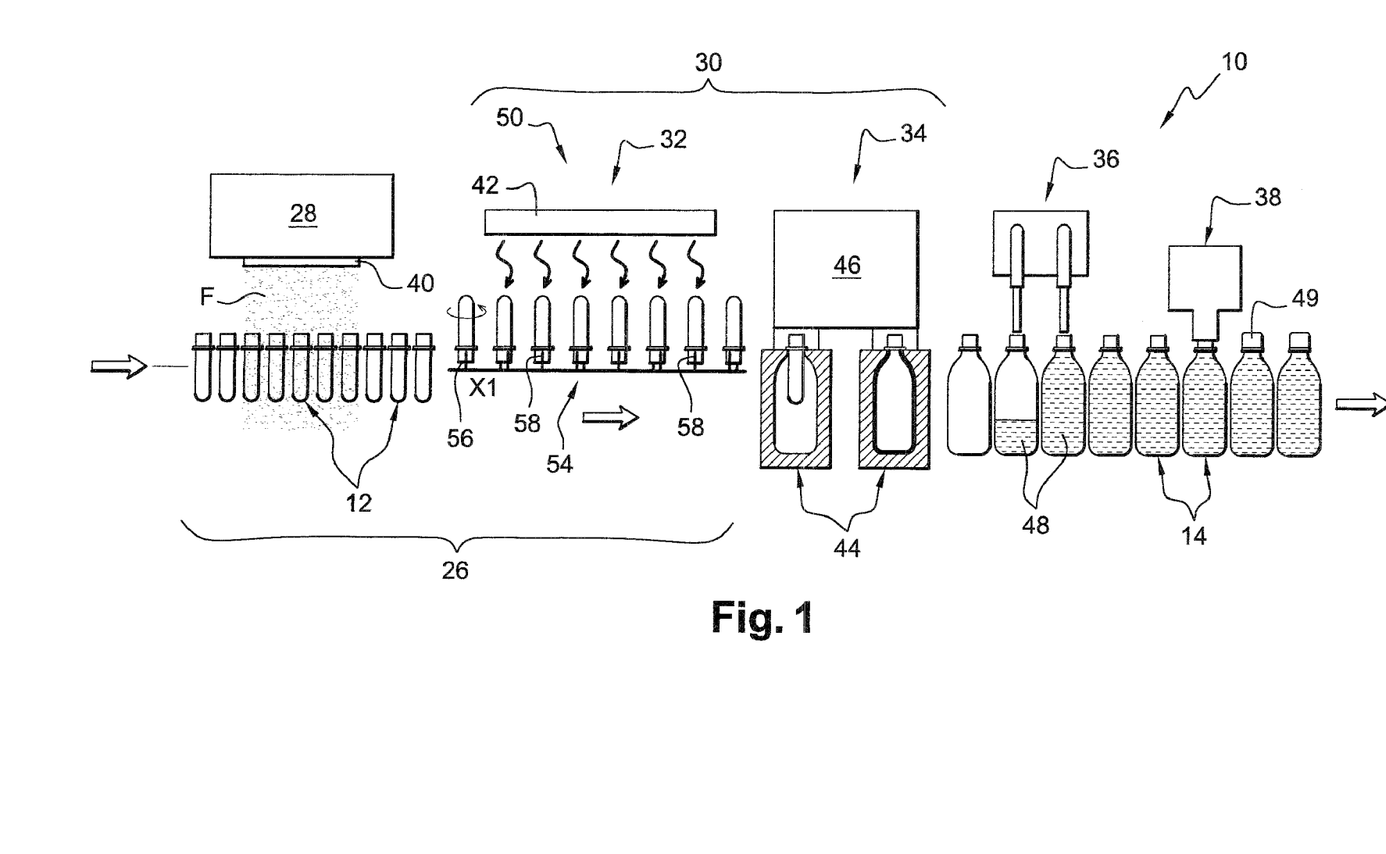
FIG. 1 shows schematically a first embodiment of an installation producing sterile bottles by blow molding and including a sterilization unit implementing the sterilization method according to the invention.

FIG. 1 shows an installation 10 producing bottles 14, in particular sterile or aseptic bottles, which are advantageously obtained by blow molding plastic preforms 12.

This type of installation 10 is for example used for the manufacture of plastic bottles 14, such as polyethylene terephthalate (PET) bottles.

Each preform 12 is overall in the form of a tube which is closed at one end, its other end already having the definitive form of the neck 16 of the bottle 14.

Figure 2:
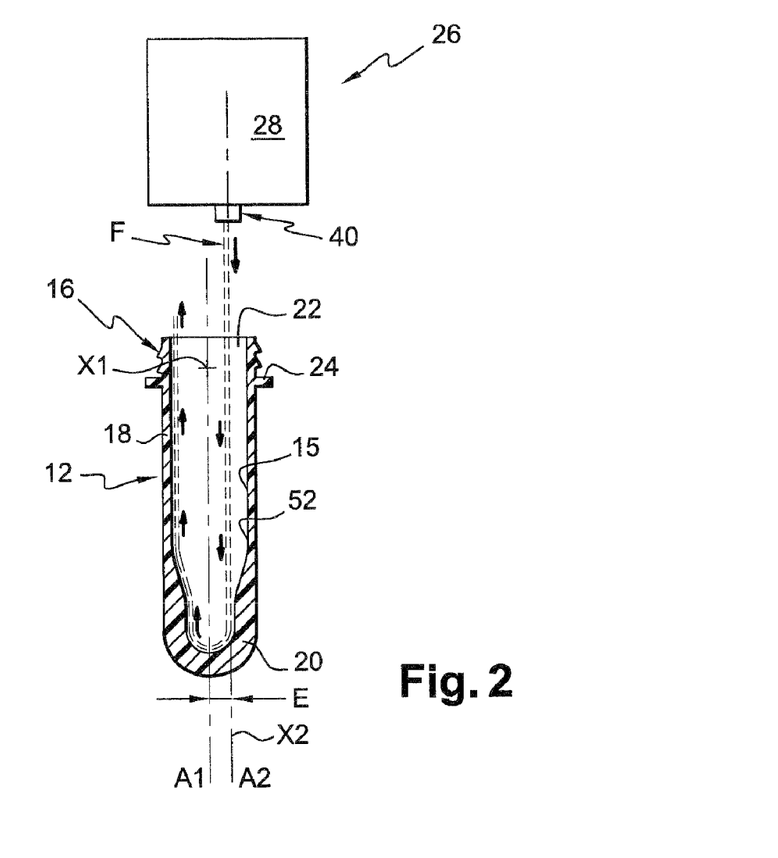
FIG. 2 is an axial sectional view in the plane of section 2-2, which shows schematically a preform in the sterilization unit of the installation of FIG. 1.

In FIG. 2, a preform 12 is shown, by way of nonlimiting example, with the axis A1 of its cylindrical body 18 extending vertically and coincident with the axis of the neck 16.

The lower end 20 of the preform 12 is closed, while its upper end forms the neck 16, which defines an inner opening 22 and is provided here with an external radial collar 24.

The preforms 12 are generally produced by an injection molding process and are for example molded on a side other than that where the installation 10 is located.

For some applications, the bottles 14 obtained from the preforms 12 must have a certain degree of sterility, and this is why it is general practice to carry out an operation to sterilize the preforms 12 in the installation 10 for producing the bottles 14.

More precisely, the sterilization operation generally relates to the neck 16 and the internal wall 15 of the preform 12 corresponding to the internal wall defining the internal volume of the bottle 14 intended to be filled.

FIG. 1 shows a first embodiment of an installation 10 employing the method of sterilizing preforms 12 according to the invention.

Conventionally, the preforms 12 are conveyed into such an installation 10 as a continuous flow running from the upstream toward the downstream end, that is to say from the left to the right when considering FIG. 1.

The installation 10 comprises, from the upstream end to the downstream end, a sterilization unit 26 for sterilizing the preforms 12, which includes at least one spray station 28, and a forming unit 30, for forming the sterilized preforms 12, which includes a thermal conditioning station 32 and a molding station 34.

Advantageously, the installation 10 also includes, after the molding station 34 of the forming unit 30, a filling unit 36 and a stoppering unit 38.

Preferably, the sterilization unit 26 includes means (not shown) for preparing the vaporized sterilizing agent with which the spray station 28 is supplied.

The spray station 28 of the sterilization unit 26 is provided with at least one nozzle 40 which, during the treatment, sprays a flow F of sterilizing agent, in the form of a vapor jet, here toward the neck 16 of each preform 12 to be sterilized.

Thus, the means for preparing the sterilizing agent comprise, for example, heating means (not shown) for heating the sterilizing agent and a supply of air (not shown), advantageously air compressed and/or sterilized by any appropriate means, which supply is designed to expel the vaporized sterilizing agent through the nozzle 40.

Advantageously, the compressed air is dehydrated and flows at low speed as a directional flow so as to constitute a carrier for the vapor of the sterilizing agent.

Preferably, the sterilizing agent consists of a compound containing hydrogen peroxide or vaporized hydrogen peroxide ($H_2O_2$) which, at the spray station 28, is sprayed toward the preforms 12 in the form of a jet of gas containing the sterilizing agent in the vapor state, advantageously a jet of dry vapor.

In accordance with the sterilization method according to the invention, in particular to sterilize the internal wall 15 of the preform 12, at least the following steps are carried out in succession:
 (a) in checking that the preform 12 is at a temperature T1 below the temperature Tc of condensation of the sterilizing agent;
 (b) in spraying a flow F of sterilizing agent in the form of a vapor jet toward the neck 16 of the preform 12 so as to cause a substantially uniform film of a mist of the sterilizing agent to be deposited by condensing on at least the internal wall 15 of the preform 12 to be sterilized; and
 (c) in radiatively heating the preform 12 thus treated in order to bring the preform 12 to a temperature T2 equal to or above the temperature Ta for activating the sterilizing agent so as to sterilize at least the internal wall 15 of the perform 12.

Advantageously, the temperature T2 is also above the evaporation temperature Te of the sterilizing agent so as to eliminate it by evaporation simultaneously with its thermal activation by radiation.

Advantageously, the condensation temperature Tc of the hydrogen peroxide is such that, when the preform 12 is at a temperature substantially equal to the ambient temperature of the installation 10, for example between 7° C. and 35° C., which means that the vaporized sterilizing agent can easily condense properly.

In addition, it is then simpler to check the temperature in step (a) since it is unnecessary to modify the temperature of the preform 12, by heating or cooling, in order for the sterilizing agent to condense on the internal wall 15 of the preform.

The sterilization unit 26 will be described in more detail below in relation to the features of the method according to the invention.

The thermal conditioning station 32 of the forming unit 30 comprises at least one oven 42 which is conventionally designed to heat the preforms 12 so as to bring them to an appropriate temperature for molding.

The molding station 34 comprises at least one mold 44 and here at least one blowing device 46 which subjects each preform 12 to an internal overpressure so that it adopts the shape of the impression of the mold 44, thereby producing a sterile bottle 14.

The molding station 34 may also include elongating means (not shown), which stretch the preform 12 toward the bottom of the mold 44 during the molding operation.

The filling unit 36 injects the product 48 to be packaged in the bottles 14 coming from the molding station 34 and then the stoppering unit 38 hermetically seals the filled sterile bottles 14 with an appropriate cap 49 or, as a variant, with a membrane and/or a stopper.

The sterilization unit 26 of the installation 10 will now be described in greater detail according to the teachings of the invention.

According to the invention, the sterilization unit 26 of the installation 10 comprises, on one side, the spray station 28 for spraying the sterilizing agent in order to carry out step (b) and, on the other side, an activation station 50 for activating the sterilizing agent in order to carry out step (c).

Thus, at the spray station 28, the flow (F) of the sterilizing agent is sprayed onto each preform 12, the temperature T1 of which is below the condensation temperature Tc of the sterilizing agent so that a film of a mist 52 of the sterilizing agent is uniformly deposited by condensing on at least the internal wall 15 and the neck 16 of the preform 12 to be sterilized.

The concentration of the vapor of sterilizing agent is for example substantially equal to twenty-five percent.

The activation station 50 for activating the sterilizing agent comprises heating means that heat by radiation, such as infrared radiation, in order to heat each preform 12 pretreated at step (a) up to a temperature T2 equal to or above the activation temperature Ta so as in particular to sterilize the internal wall 15 of the preform 12.

On leaving the nozzle 40, the vapor containing the sterilizing agent reaches a given temperature T substantially above the evaporation temperature Te of the sterilizing agent so that the vapor of sterilizing agent instantly condenses on the preform 12.

In the case when hydrogen peroxide ($H_2O_2$) is used, the temperature T at the nozzle exit is advantageously above one hundred and six degrees Celsius (106° C.), preferably between one hundred and ten degrees Celsius (110° C.) and one hundred and twenty degrees Celsius (120° C.).

When this vapor comes into contact with each preform 12, which is colder, the vaporized sterilizing agent condenses so that the entire preform 12, in particular the internal wall 15, is then imbued with a film of sterilizing agent mist 52.

The nozzle 40 here is made so that the substantially uniform film of mist 52 is deposited mainly on the neck 16 and on the entire surface of the internal wall 15 of the preform 12.

Advantageously, the condensation deposition as a uniform film of a mist 52 of the sterile product makes it possible, compared with the prior art, to eliminate any risk of stains or "orange peel" effects appearing.

The heating means of the sterilizing agent activation station consists for example of a radiation heating oven having heating elements.

Advantageously, the heating means of the activation station 50 consist here of the oven 42 of the thermal conditioning station 32.

Thus, the preform 12 is heated so as to reach a molding temperature Tm which, depending on the type of preform, may vary between 95° C. and 135° C., which here is above the activation temperature Ta of the sterilizing agent and above the evaporation temperature Te, respectively, making it possible at the same time to eliminate the sterilizing agent by evaporation.

This is because the activation temperature Ta of hydrogen peroxide ($H_2O_2$) is about seventy degrees Celsius (70° C.), i.e. here a temperature below the molding temperature Tm since the molding temperature Tm is for example between ninety-five degrees Celsius (95° C.) and one hundred and five degrees Celsius (135° C.).

Of course, the molding temperature Tm depends on the type of preform 12, this type being determined according to the applications and the containers or bottles 14.

As is known, the oven 42 has the function in the thermal conditioning unit 32 of reheating the preforms 12 to a temperature above the molding temperature (95° C. to 135° C.) so as thereafter to be able to carry out the molding operation in the molding station 34, especially by blow molding the sterilized preform 12.

However, since the radiation heating oven 42 here is common to the activation station 50 and the thermal conditioning station 32, it therefore has two functions in the installation 10.

Specifically, the oven 42 by heating, causes, on the one hand, the condensed sterilizing agent to be activated, which has an immediate bactericidal effect on the internal wall 15 of the preforms 12, and, on the other hand, the heating of the preform 12 so that it can be molded by blow molding so as to obtain the desired sterile bottle 14.

Furthermore, since the molding temperature Tm is above the evaporation temperature Te, the sterilizing agent is automatically eliminated by evaporation, without requiring additional means.

In a known manner (not shown), such a heating oven 42 generally comprises a longitudinal heating tunnel, along which the preforms 12 are transported by a transport device 54, also called a "spinner", between a first end of the tunnel where the preforms 12 enter cold, before emerging via the second end of the tunnel heated or reheated, ready for the blowing/molding operation.

Moreover, one wall of the tunnel is equipped with radiative heating means, such as infrared lamps, while the other wall is provided with aeration orifices to allow the blown air to pass so as to favor uniform heating throughout the thickness of the preform 12 without overheating the layer of surface material.

This is because the blown air makes it possible for the convective heat caused by the heating means to be removed in order to favor penetration of the radiation that they produce in the thickness of the material constituting the preform 12.

For details about such ovens 42 for heating the preforms, the reader may for example refer to the following documents: EP-A-0 620 099 or EP-A-0 564 354.

Preferably, the oven 42 includes protection means, especially for limiting the corrosion of the parts or components exposed to the sterile product which, by evaporating from the preforms 12, is thus blown into the tunnel.

Advantageously, the transport device 54 is provided with means 56 for gripping the neck 16 of each preform 12 in order to convey the flow of preforms 12 into the oven 42.

Document WO-A-00/48819, to which the reader may refer for further details, describes an example of a transport device 54 of this type, which advantageously includes means for making the preforms 12 rotate about themselves during their passage through the oven 42 so as to ensure depthwise heating of the preform 12, that is to say both at the lower end 20 forming the bottom and the cylindrical body 18.

The transport device 54 includes at least one means, such as an internal core 58, also called a "spinner nose", which penetrates axially into the neck 16 of each preform 12, completely or partly obstructing the inner opening 22 bounded the neck 16, so as to increase the degree of sterilization by increasing the time over which the internal wall 15 of the preform 12 is exposed to the sterilizing agent.

However, in the case of an installation 10 as shown in FIG. 1, the air blown over each preform 12 in the oven 42 removes all or some of the film of mist 52 that can also be deposited by condensing on the external wall of the preform 12 in the spray station 28 of the sterilization unit 26.

This is one of the reasons, together with the fact that sterility of the external wall is not in general desired, why the aim of the sterilization unit 26 is essentially to sterilize the neck 16 and the internal wall 15.

Thus, as will have been understood, what are therefore obtained on leaving the oven 42 are preforms 12 that are mainly sterile on the inside and that have advantageously to remain sterile right to the final stoppering operation.

In one embodiment (not shown) of the installation 10, a sterile confinement chamber may be provided for controlling and maintaining the sterility of the sterilized preforms 12 and of the bottles 14 between the various units or stations of the installation.

Thanks to an installation 10 according to FIG. 1, a logarithmic reduction in the number of germs of the order of 3 decimal or 3 log equivalent to 1000 units ($10^3$).

The number of germs is for example counted in a known manner, by counting them after washing, filtering and culturing operations.

Figure 3:
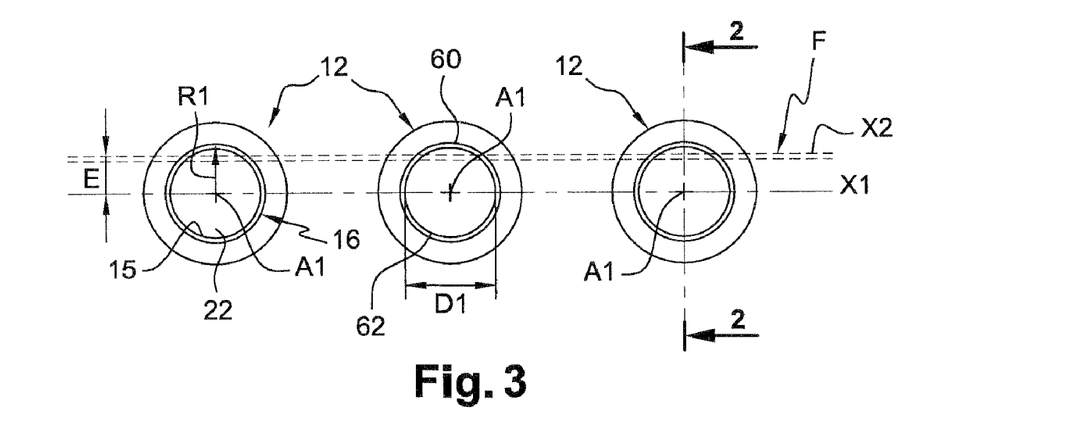
FIG. 3 is a top view showing a series of preforms at the spray station of the sterilization unit.

According to the embodiment shown here, in particular in FIG. 3, the preforms 12 run through the spray station 28 of the sterilization unit 26 in that they are aligned, in a vertical position, along a longitudinal horizontal direction, called the run direction X1, the neck 16 being uppermost.

The run direction X1 passes through the axes A1 of the preforms 12 undergoing treatment.

Advantageously, the mean spray axis A2 of the nozzle 40 is generally parallel to the axis A1 of each preform 12 undergoing treatment, and this axis A2 is radially offset relative to the axis A1 of the preform 12 by a defined offset E.

Preferably, the mean spray axis A2, which here is vertical, is off-center along an internal radius R1 of the neck 16, which is orthogonal to the run direction X1.

Thus, the shape of the nozzle 40 makes it possible to spray a flow F of sterilizing agent downward generally in the form of a laminar flow, that is to say in the form of a longitudinal vertical curtain. For this purpose, the nozzle 40 has for example a longitudinal slot or a generally circular hole for spraying the flow F.

The laminar flow F here lies generally in a longitudinal vertical plane, called the spray plane X2, which is radially offset relative to the run direction X1 by a distance equal to the offset E.

The flow F of sterilizing agent admits here an infinity of mean spray axes A2, which lie vertically in the spray plane X2.

Preferably, the offset E is between a minimum $E_{min}$ approximately equal to nineteen percent of the inside diameter D1 of the neck 16 of each preform 12 and a maximum $E_{max}$ approximately equal to thirty-two percent of the inside diameter D1 of the neck 16.

According to one advantageous embodiment, the offset E is chosen to be fixed and approximately equal to eight millimeters, so that it is convenient for models of preforms 12 having inside diameters D1 ranging between about twenty-five and forty-two millimeters.

Thanks to such an arrangement of the nozzle 40, the flow F of sterilizing agent is substantially flush with a first sector 60 of the internal wall 15 of each preform 12 so that the flow F of sterilizing agent licks said sector 60 of the internal wall 15.

On arriving at the lower end 20 of the preform 12, the flow F of sterilizing agent slides over the bottom of the preform 12 and rises up along a second sector 62 of the internal wall 15, diametrically opposite the first sector 60.

Thus, the flow F of sterilizing agent generally sweeps over the entire internal wall 15 of each preform 12 by a laminar-type flow.

Such an arrangement makes it possible in particular to prevent the formation of an overpressure plug in the bottom of the preforms 12, which would prevent the sterilizing agent from reaching the bottom.

In particular, the spray rate of the sterilizing agent on leaving the nozzle 40 is low enough to allow laminar flow.

It should be noted that the flow F of sterilizing agent creates a mist of vaporized sterilizing agent which diffuses all around the flow F, allowing the sterilizing agent to be deposited over the entire area of each preform 12 and thus simultaneously sterilizing or aseptizing the neck 16, the internal wall 15 and the external wall of each preform 12.

Figure 4:
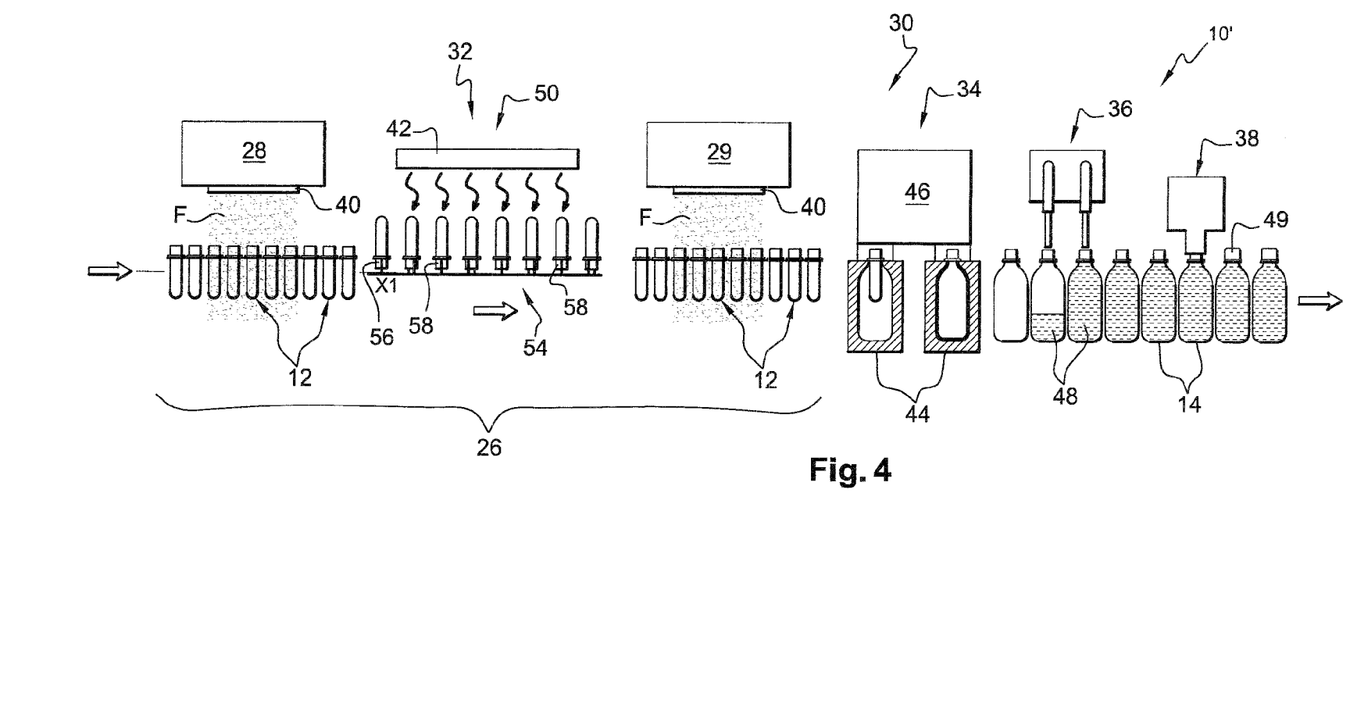
FIG. 4 shows schematically a second embodiment of an installation producing sterile bottles by blow molding and including a sterilization unit that includes a first spray station for implementing the sterilization method according to the invention and a second spray station.

A second embodiment of an installation 10' employing the preform sterilization method according to the invention will be described below in comparison with the installation 10 of FIG. 1.

FIG. 4 shows an installation 10' capable of producing sterile bottles by blow molding preforms sterilized in accordance with the invention.

The preforms 12 are conveyed through the installation 10' as a continuous flow that runs from the upstream end toward the downstream end, that is to say from the left to the right when considering FIG. 4.

The installation 10' according to FIG. 4 differs mainly from the installation 10 according to FIG. 1 in that the sterilization unit 26 includes an additional spray station 29, called the second spray station.

The second spray station 29 is placed downstream of the thermal conditioning station 32 of the forming unit 30 formed by the oven 42, which combines the function of the activation station 50 of the sterilization unit 26.

The installation 10' comprises, from the upstream end toward the downstream end: a first sterilization unit 26 for sterilizing the preforms 12, comprising what is called the first spray station 28; an activation station 50 formed by the oven 42; a second spray station 29; then a forming unit 30 for forming the preforms 12, comprising a thermal conditioning station 32 and a molding station 34.

Advantageously, the installation 10' includes, downstream of the molding station 34 of the forming unit 30, a filling unit 36 and a stoppering unit 38.

The stations 28, 32, 50 and 34 and the units 36, 38 are analogous to those of FIG. 1 described above.

Preferably, the sterilization unit 26 includes means (not shown) for preparing the vaporized sterilizing agent in order for the first spray station 28 and/or the second spray station 29 to be supplied.

The second spray station 29 of the sterilization unit 26 is, like the first station 28, provided with at least one nozzle 40 which sprays, during the treatment, a flow F of sterilizing agent in the form of a jet of vapor, here toward the neck 16 of each preform 12 to be sterilized.

Thus, the means for preparing the sterilizing agent comprise for example means (not shown) for heating the sterilizing agent and a source (not shown) of air, advantageously air that is compressed and/or sterilized by any appropriate means, which is designed to expel the vaporized sterilizing agent through the nozzle 40.

Advantageously, the compressed air is dehydrated and flows at low speed as a directional flow so as to form a carrier for the sterilizing agent vapor.

Preferably, the sterilizing agent consists of a compound containing hydrogen peroxide or vaporized hydrogen peroxide ($H_2O_2$) which, in the second spray station 29, is sprayed onto the preforms 12 in the form of a jet of gas containing sterilizing agent in the vapor state, advantageously a jet of dry vapor.

In accordance with the sterilization method according to the invention, steps (a), (b) and (c) are carried out in succession so as to sterilize at least the internal wall 15 and the neck 16 of the preform 12 with a logarithmic reduction in the number of germs of the order of 3 decimal or 3 log.

Thus, as previously, deposition step (b) is carried out, by making a uniform film of sterilizing agent mist condense in the first spray station 26, and then step (c) of heating the preform 12 in the activation station 50 for activating the sterilizing agent is carried out.

In the first spray station 28, the flow F of sterilizing agent is therefore vaporized on each preform 12 which is, in accordance with step (a), at a temperature T1 below the condensation temperature Tc of the sterilizing agent.

In the station 50 for activating the sterilizing agent, the preforms 12 are therefore at least heated to a temperature T2, preferably equal to or above the molding temperature Tm and at the very least equal to or above the activation temperature Ta.

Advantageously, the oven 42 of the thermal conditioning station 32 constituting the radiative heating means of the activation station 50 raises each preform 12 directly to the molding temperature Tm, which is above the activation temperature Ta of the sterilizing agent and here above the evaporation temperature Te, so as to eliminate it by evaporation.

Advantageously, the heating oven 42 simultaneously exerts in the installation 10' the function of the thermal conditioning station 32 and the function of the activation station 50, both for the first spray station 28 and for the second spray station 29.

The second spray station 29 of the sterilization unit 26, which is intended to treat the preforms 12 in an additional sterilization step so as to achieve, both on the internal wall 15 and on the neck 16, a logarithmic reduction in the number of germs, which is either greater than 3 decimal or 3 log, will be described below in greater detail.

After the preforms 12 have been heated by the oven 42 of the stations 32, 50 to the defined temperature T2, they then pass directly into the second spray station 29 located downstream in order to undergo therein the additional sterilization step (d).

Advantageously, the heating temperature T2 is equal to or above the molding temperature Tm, for example between ninety-five degrees Celsius (95° C.) and one hundred and thirty-five degrees Celsius (135° C.).

Now, since the preforms 12 are at a temperature above the activation temperature Ta, for example of the order of about seventy degrees Celsius (70° C.) in the case of hydrogen peroxide ($H_2O_2$), within the second spray station 29 there is no deposition by the condensing of a uniform film of a mist of the sterilizing agent as previously in the first spray station 28.

This is because the sterilizing agent is instantly activated and evaporates on contact with the heated preform 12, consequently producing a similar bactericidal effect on the entire area of the preform 12, that is to say both on the internal wall 15 and the neck 16 and on the external parts of the preform 12.

Thanks to the additional sterilization step carried out in the second spray station 29, a logarithmic reduction in the number of germs of at least the order of 5D or 5 log is advantageously achieved.

The preforms 12 traveling through the installation 10, 10', especially the sterilization unit 26, are here oriented vertically with the neck 16 uppermost, that is to say in the "neck up" position.

As a variant, the preforms 12 are oriented vertically with the neck 16 downmost, i.e. "neck down", it being possible for the preforms 12 to change vertical orientation within the installation 10, 10', in particular from one unit or station to another.

The installation 10, 10' therefore includes here transfer means (not shown) that can invert the preforms 12 treated in the spray station 28 of the sterilization unit 26 in the "neck up" position to a "neck down" position in order to be taken up by the transport device 54 associated with the oven 42.

It should be noted that the installation 10, 10' has been shown with treatment units such as the sterilization unit 26, the forming unit 30, the filling unit 36 and the stoppering unit 38.

These units are shown aligned, by way of illustration, but these units may be arranged in a different configuration, especially with rotating devices such as carousels (not shown).

The invention claimed is:

1. A sterilization method, for sterilizing a plastic preform intended to be molded, especially by blow molding, in an installation (10, 10') producing sterile bottles (14), which method is characterized in that it comprises at least the steps consisting, in succession:
   (a) in checking that the preform (12) is at a temperature (T1) below the temperature (Tc) of condensation of the sterilizing agent;
   (b) in spraying a flow (F) of sterilizing agent in the form of a vapor jet onto the preform (12) so as to cause a substantially uniform film of a mist (52) of the sterilizing agent to be deposited by condensing on at least one internal wall (15) of the preform to be sterilized; and
   (c) in radiatively heating the preform (12) thus treated in order to bring it to a temperature (T2) equal to or above the temperature (Ta) for activating the sterilizing agent so as to sterilize at least the internal wall (15) of the preform.

2. The sterilization method as claimed in claim 1, characterized in that it includes an additional sterilization step consisting:
   (d) in spraying a flow (F) of sterilizing agent in the form of a jet of vapor onto the preform (12) preheated to the specified temperature (T2).

3. A sterilization method, for sterilizing a plastic preform intended to be molded, especially by blow molding, in an installation (10, 10') producing sterile bottles (14), which method is characterized in that it comprises at least the steps consisting, in succession:
   (a) in checking that the preform (12) is at a temperature (T1) below the temperature (Tc) of condensation of the sterilizing agent;
   (b) in spraying a flow (F) of sterilizing agent in the form of a vapor jet onto the preform (12) so as to cause a substantially uniform film of a mist (52) of the sterilizing agent to be deposited by condensing on at least one internal wall (15) of the preform to be sterilized; and
   (c) in radiatively heating the preform (12) thus treated in order to bring it to a temperature (T2) equal to or above the temperature (Ta) for activating the sterilizing agent so as to sterilize at least the internal wall (15) of the perform,
   characterized in that the temperature (T2) to which the preform (12) is heated is substantially equal to the temperature (Tm) at which the preform (12) is blow-molded, which temperature is respectively above the activation temperature (Ta) and above the evaporation temperature (Te) in order to eliminate the sterilizing agent by evaporation.

4. The sterilization method as claimed in claim 2, characterized in that the temperature (T2) to which the preform (12) is heated is substantially equal to the temperature (Tm) at which the preform (12) is blow-molded, which temperature is respectively above the activation temperature (Ta) and above the evaporation temperature (Te) in order to eliminate the sterilizing agent by evaporation.

* * * * *